US010641768B2

(12) United States Patent
Yoshimura et al.

(10) Patent No.: US 10,641,768 B2
(45) Date of Patent: May 5, 2020

(54) METHODS AND KITS FOR DECREASING INTERFERENCES FROM LEUKOCYTES IN SPECIFIC BINDING ASSAYS

(75) Inventors: Toru Yoshimura, Chiba (JP); Kenju Fujita, Chiba (JP)

(73) Assignee: ABBOTT JAPAN CO. LTD., Matsudo-Shi Chiba (JP)

( * ) Notice: Subject to any disclaimer, the term of this patent is extended or adjusted under 35 U.S.C. 154(b) by 11 days.

(21) Appl. No.: 13/178,638

(22) Filed: Jul. 8, 2011

(65) Prior Publication Data
US 2013/0011826 A1 Jan. 10, 2013

(51) Int. Cl.
*G01N 33/53* (2006.01)
*G01N 33/543* (2006.01)

(52) U.S. Cl.
CPC . *G01N 33/54393* (2013.01); *G01N 33/54333* (2013.01); *G01N 2333/902* (2013.01)

(58) Field of Classification Search
None
See application file for complete search history.

(56) References Cited

U.S. PATENT DOCUMENTS

| 4,434,150 A * | 2/1984 | Azad | G01N 33/532 |
| | | | 252/645 |
| 4,780,410 A * | 10/1988 | Matsuda | G01N 33/86 |
| | | | 435/13 |
| 5,006,309 A | 4/1991 | Khalil et al. | |
| 5,076,950 A * | 12/1991 | Ullman | B03C 1/01 |
| | | | 210/222 |
| 5,089,424 A | 2/1992 | Khalil et al. | |
| 5,177,292 A | 1/1993 | Lenglet et al. | |
| 5,241,070 A | 8/1993 | Law | |
| 5,244,630 A | 9/1993 | Khalil et al. | |
| 5,468,646 A | 11/1995 | Mattingly et al. | |
| 5,516,640 A * | 5/1996 | Watanabe | G01N 33/57438 |
| | | | 435/13 |
| 5,543,524 A | 8/1996 | Mattingly et al. | |
| 5,783,699 A | 7/1998 | Mattingly et al. | |
| 7,488,608 B2 * | 2/2009 | Teng et al. | 436/529 |
| 7,723,099 B2 * | 5/2010 | Miller et al. | 435/287.1 |
| 2005/0170362 A1 * | 8/2005 | Wada et al. | 435/6 |
| 2007/0148640 A1 * | 6/2007 | Scopp | G01N 33/5306 |
| | | | 435/5 |
| 2010/0233175 A1 * | 9/2010 | Yoshimura | C07K 16/40 |
| | | | 424/139.1 |
| 2011/0014602 A1 * | 1/2011 | Kim | C12Q 1/6886 |
| | | | 435/6.14 |
| 2011/0306070 A1 * | 12/2011 | Campbell et al. | 435/7.93 |
| 2011/0306513 A1 * | 12/2011 | Song | C12Q 1/6886 |
| | | | 506/9 |

FOREIGN PATENT DOCUMENTS

| EP | 0424634 A2 | 5/1991 | |
| WO | WO 03031977 A2 * | 4/2003 | |
| WO | WO 2006125124 A2 * | 11/2006 | G01N 33/54353 |

OTHER PUBLICATIONS

Serres et al., "Affinity of mouse immunoglobulin G subclasses for sialic acid derivatives immobilized on dextran-coated supports," Journal of Chromatography B. 681: pp. 219-226 (1996).*
Baek et al., "Diagnostic role and correlation with staging systems of PIVKA-II compared with AFP," Hepatogasterenterology, 56 (91-92): pp. 763-767 (2009).*
Decker et al., "Mechanism and Specificity of L- and D-6-Hydroxynicotine Oxidase," European J. Biochem. 3: pp. 132-138 (1967).*
PDF of Compound 122322-03-6 from Mattingly et al. (U.S. Pat. No. 5,468,646).*
Skoog et al., "Studies on the Fibrinogen, Dextran and Phytohemagglutinin Methods of Isolating Leukocytes," Blood 11(5): 436-54 (1956).*
Truzzolillo et al., "Dielectric properties of differently flexible polyions: a scaling approach," Phys. Chem. Chem. Phys. 11: 1780-1786 (2009).*
Adamczyk M., et al., "Chemiluminescent N-Sulfonylacridinium-9-Carboxamides and Their Application in Clinical Assays," Luminescence Biotechnology: Instruments and Applications, 2002, pp. 77-105.
Adamczyk M., et al., "Linker-Medicated Modulation of the Chemiluminescent Signal From $N^{10}$-(3-Sulfopropyl)-N-Sulfonylacridinium-9-Carboxamide Tracers," Bioconjugate Chemistry, 2000, vol. 11, pp. 714-724.
Adamczyk M., et al., "Modulation of the Chemiluminescent Signal From $N^{10}$-(3-Sulfopropyl)-N-Sulfonylacridinium-9-Carboxamides," Tetrahedron, 1999, vol. 55, pp. 10899-10914.
Adamczyk M., et al., "Neopentyl 3-Triflyloxypropanesulfaonate. A Reactive Sulfopropylation Reagent for the Preparation of Chemiluminescent Labels," Journal of Organic Chemistry, 1998, vol. 63, pp. 5636-5639.
Adamczyk M., et al., "Regiodependent Luminescence Quenching of Biotinylated N-Sulfonyl-Acridinium-9-Carboxamides by Avidin," Organic Letters, 2003, vol. 5 (21), pp. 3779-3782.
Adamczyk M., et al., "Synthesis of a Chemiluminescent Acridinium Hydroxylamine (AHA) for the Direct Detection of Abasic Sites in DNA," Organic Letters, 1999, vol. 1 (5), pp. 779-781.
Asai D.J., "Antibodies in Cell Biology" in: Methods in Cell Biology, vol. 37, Academic Press Inc., 1993, Table of Contents.
Coligan J.E., et al., "Peptides" in: Current Protocols in Immunology, John Wiley & Sons, 1991, Table of Contents.
Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.
Kohler G., et al., "Continuous Cultures of Fused Cells Secreting Antibody of Predefined Specificity," Nature, 1975, vol. 256 (5517), pp. 495-497.
Mattingly P.G., "Chemiluminescent 10-Methyl-Acridinium-9(N-Sulphonylcarboxamide) Salts. Synthesis and Kinetics of Light Emission," Journal of Bioluminescence and Chemiluminescence, 1991, vol. 6, pp. 107-114.

(Continued)

*Primary Examiner* — M Franco G Salvoza

(74) *Attorney, Agent, or Firm* — Casimir Jones, S.C.; Melissa E. Kolom

(57) ABSTRACT

The present disclosure describes methods and kits for reducing interferences in immunoassays performed on solid phase and on samples containing serum or plasma, by adding an effective amount of a polycationic derivative of dextran to the assay.

11 Claims, No Drawings

(56) References Cited

OTHER PUBLICATIONS

McCafferty J., et al., "Phage Antibodies: Filamentous Phage Displaying Antibody Variable Domains," Nature, 1990, vol. 348, pp. 552-554.
McCapra F., et al., "Chemiluminescence Involving Peroxide Decompositions," Photochemistry and Photobiology, 1965, vol. 4, pp. 1111-1121.
Razavi Z., et al., "Stable and Versatile Active Acridinium Esters I," Luminescence, 2000, vol. 15 (4), pp. 239-244.
Razavi Z., et al., "Stable and Versatile Active Acridinium Esters II," Luminescence, 2000, vol. 15, pp. 245-249.
Stites D.P., et al., "Basic and Clinical Immunology," 7th Edition, Appleton & Lange, 1991, Table of Contents.
Vaitukaitis J.L., "Production of Antisera with Small Doses of Immunogen: Multiple Intradermal Injections," Methods in Enzymology, 1981, vol. 73 (Pt B), pp. 46-52.

\* cited by examiner

METHODS AND KITS FOR DECREASING INTERFERENCES FROM LEUKOCYTES IN SPECIFIC BINDING ASSAYS

RELATED APPLICATION INFORMATION

None.

TECHNICAL FIELD

The present disclosure relates generally to assays and kits for detecting a target analyte in a test sample, and in particular to immunoassay methods and kits for improving detection of an analyte when interference from leukocytes in test samples produces inaccurate assay results.

BACKGROUND OF THE INVENTION

Immunoassay techniques have been known for the last few decades and are now commonly used in medicine for a wide variety of diagnostic purposes to detect target analytes in a biological sample. Immunoassays exploit the highly specific binding of an antibody to its corresponding antigen, wherein the antigen is the target analyte. Typically, quantification of either the antibody or antigen is achieved through some form of labeling such as radio- or fluorescence-labeling. Sandwich immunoassays involve binding the target analyte in the sample to the antibody site (which is frequently bound to a solid support), binding labeled antibody to the captured analyte, and then measuring the amount of bound labeled antibody, wherein the label generates a signal proportional to the concentration of the target analyte inasmuch as labeled antibody does not bind unless the analyte is present in the sample.

Immunoassay methods can be carried out in any of a wide variety of formats. A typical heterogeneous sandwich immunoassay employs a solid phase as a support to which is bound a first (capture) antibody reactive with at least one epitope on the target analyte. A second (detection) antibody is also reactive with at least one epitope the target analyte, and may be conjugated to a detectable label that provides a signal that is measured after the detection antibody binds to the captured target analyte. The solid phase is made of a material with sufficient surface affinity to bind an antibody and can take many different forms, including a magnetic or paramagnetic microparticle composed of a suitable polymer. These magnetic or paramagnetic microparticles are used to facilitate manipulation of the microparticle within a magnetic field, so that they can be separated from a mixture of soluble reagents and a test sample using the magnetic field.

Whole blood samples are often prepared for assay by centrifuging the sample, resulting in the formation of three layers: a clear fluid layer (plasma at the top), a red fluid layer at the bottom that contains most of the erythrocytes (red blood cells), and a thin dividing buffy coat layer between the plasma layer and erythrocyte layer, which contains most of the leukocytes (white blood cells) and platelets. When centrifuging is insufficient, the layers are not completely separated and, depending on the extent and quality of centrifuging, the plasma layer may contain substantial amounts of leukocytes and platelets. Magnetic- and paramagnetic-particle based assays targeting analytes in blood serum or plasma are subject to interference from leukocytes that may remain in the plasma layer due to incomplete separation of the layers. For example, assays can provide lower than expected values when test samples are not sufficiently centrifuged in preparation for the assay, due to interference from leukocytes remaining in the plasma layer. The interference problem increases the risk of false negative diagnostic results and the risk that individuals will not obtain a timely diagnosis.

One approach to the interference problem involves adding poly-L-Lysine directly to the assay system, notwithstanding the recognition that doing so may interfere with the system by aggregating other reagents and binding members in addition to the red blood cells. The addition of poly-L-lysine is thus not always effective, particularly when a poly-anion material is used in the reaction solution. Moreover, poly-L-Lysine is costly.

Improved immunoassay methods and kits are needed, which compensate for interference from various substances such as leukocytes that may also be present in a test sample, and in particular for such methods that do so at minimal cost and without contributing another source of interference to the assay system.

SUMMARY OF THE INVENTION

In one aspect, the present disclosure provides a method for decreasing interferences in a specific binding assay of a test sample containing serum or plasma, comprising adding an effective amount of a polycationic derivative of dextran to the specific binding assay. The specific binding assay is performed, for example, on a solid phase which can be magnetic or paramagnetic microparticles. In this method and in any of the methods of the present disclosure, the polycationic derivative of dextran can be, for example, diethylaminoethyl-dextran (DEAE-dextran). In any of the methods, the specific binding assay may measure a target analyte such as, for example, thyroid stimulating hormone, luteinizing hormone, free prostate specific antigen, alpha fetal protein, Hepatitis B core antibody, Hepatitis B surface antibody, human immunodeficiency virus or PIVKA-II.

In another aspect, the present disclosure provides a method for decreasing interferences in a specific binding assay of a test sample containing serum or plasma, comprising, in a specific binding assay for a target analyte, adding a polycationic derivative of dextran to one or more test samples containing serum or plasma during incubation of the one or more serum- or plasma-containing samples with a solid phase coated with a first antibody capable of specifically binding the target analyte.

In another aspect, the present disclosure provides a method for decreasing interferences in a specific binding assay of a test sample containing serum or plasma comprising, in a specific binding assay for a target analyte, (a) forming a first complex by incubating the serum or plasma sample with paramagnetic microparticles coated with a first antibody capable of specifically binding to the target analyte, and an assay diluent comprising a polycationic derivative of dextran, for a time and under conditions sufficient to allow the target analyte present in the sample to bind to the antibody coated microparticles; (b) forming a second complex by incubating the first complex with an acridinium labeled conjugate comprising an acridinium compound attached to a second antibody capable of specifically binding to the target analyte, for a time and under conditions sufficient to allow the conjugate to bind to the first complex; (c) creating a chemiluminescent reaction in the second complex; and (d) measuring the chemiluminescent reaction as relative light units wherein the amount of target analyte in the plasma or serum sample is directly related to the measured relative light units. The polycationic derivative of dextran can be DEAE-dextran. In the method, the specific binding assay can be performed on a solid phase, which can comprise magnetic or paramagnetic microparticles. In the method, step (c) can comprise, for example, i) providing a source of hydrogen peroxide to the antibody-antigen complexes; and ii) adding a basic solution to the mixture of step (i); wherein step (d) of the method comprises measuring the light signal generated or emitted following step (ii), thereby measuring the amount of antigen in the sample. In the method, the basic solution can be a solution having a pH of at least about 10. The source of hydrogen peroxide can be a buffer or a solution containing hydrogen peroxide. In an exemplary method, the source of hydrogen peroxide is a hydrogen peroxide generating enzyme. The hydrogen peroxide generating enzyme can be selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate (D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α, β-oxidase, urate oxidase (uricase, uric acid oxidase), vanillyl-alcohol oxidase, xanthine oxidase, xylitol oxidase and combinations thereof. Further, in the method the first antibody and the second antibody can independently be a polyclonal antibody, a monoclonal antibody, a chimeric antibody, a human antibody, and an affinity maturated antibody.

In another aspect, the present disclosure provides a kit for a specific binding assay of a sample containing plasma or serum, the kit comprising a solution containing a polycationic derivative of dextran and instructions for quantifying the amount of a target analyte in the sample. In the kit, the polycationic derivative of dextran can be, for example, DEAE-dextran. The kit may further comprise a solid phase. The solid phase can comprise, for example, microparticles and a first antibody capable of specifically binding a target analyte, wherein the microparticles are coated with the first antibody. The microparticles can be magnetic or paramagnetic microparticles. In the kit, the first antibody can comprise an antibody capable of specifically binding one of thyroid stimulating hormone, luteinizing hormone, free prostate specific antigen, alpha fetal protein, Hepatitis B core antibody, Hepatitis B surface antibody and human immunodeficiency virus. The first antibody can comprise, for example, a mouse, monoclonal anti-β TSH antibody, and the second antibody can comprise a mouse, monoclonal anti-α TSH antibody. The kit may further comprise an acridinium-labeled conjugate comprising an acridinium compound attached to a second antibody capable of specifically binding the target analyte. A kit containing an acridinium-labeled conjugate may further comprise a source of hydrogen peroxide and a basic solution. The basic solution can be for example a solution having a pH of at least about 10. The source of hydrogen peroxide can be a buffer, or can be a solution containing hydrogen peroxide. Alternatively, the source of hydrogen peroxide can be a hydrogen peroxide generating enzyme. The hydrogen peroxide generating enzyme can be selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate (D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α, β-oxidase, urate oxidase (uricase, uric acid oxidase), vanillyl-alcohol oxidase, xanthine oxidase, xylitol oxidase and combinations thereof.

In any of the disclosed methods or kits using an acridinium compound, the acridinium compound can be an acridinium-9-carboxamide having a structure according to formula I:

I

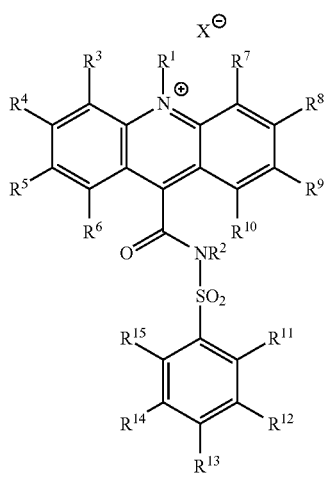

wherein R¹ and R² are each independently selected from the group consisting of: alkyl, alkenyl, alkynyl, aryl or aralkyl, sulfoalkyl, carboxyalkyl and oxoalkyl, and wherein R³ through R¹⁵ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, X$^\ominus$ is an anion.

Alternatively, in any of the disclosed methods or kits using an acridinium compound, the acridinium compound can be an acridinium-9-carboxylate aryl ester having a structure according to formula II:

II

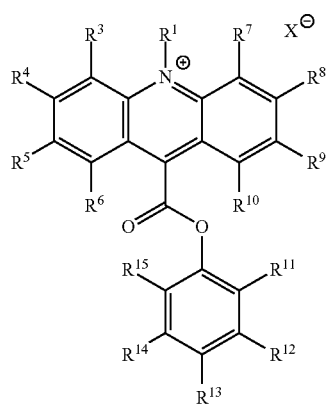

wherein R¹ is an alkyl, alkenyl, alkynyl, aryl or aralkyl, sulfoalkyl, carboxyalkyl and oxoalkyl; and wherein R³ through R¹⁵ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, X$^\ominus$ is an anion.

Any of the disclosed methods and kits can be adapted for use in an automated system or semi-automated system.

DETAILED DESCRIPTION

The present disclosure provides improved assay methods that prevent interference from leukocytes when assaying a biological sample that contains plasma or serum. The methods do not require the use of poly-L-Lysine. The methods and systems described herein are based in part on the finding that interference in magnetic microparticle-based assays is caused by leukocytes that should be isolated in the buffy coat layer of whole blood samples properly prepared by density gradient centrifugation, but instead remain in the plasma layer used for the assay. In particular, leukocytes were found to adhere to the surface of the magnetic microparticles used in the assay, and thus to inhibit the important magnetic attraction between the microparticles and magnet used in the assay process.

One possible solution to the problem of leukocyte interference is the addition of poly-L-lysine to the assay, but poly-L-lysine is costly and may introduce its own source of interference. For example, in ARCHITECT® assays (e.g., for TSH or PIVKA-II) poly-L-lysine interacts with polyanion used the assay diluent. Moreover, some types of protease that may be present in a sample due to contamination, e.g., from an animal protein source such as BSA, can degrade poly-L-lysine. Thus, according to the present disclosure, DEAE-dextran was surprisingly identified as a material that can bind to the surface of leukocytes but not interact with any polyanion material included in the assay diluent, thereby successfully improving the accuracy of the assay by preventing interference from the leukocytes while not contributing another source of interference. Additionally, DEAE-dextran is not degraded by protease, and the cost of DEAE-dextran is a small fraction of the cost of poly-L-lysine. The assay methods as described herein can be applied to any assay system that uses a magnetic or paramagnetic surface, such as microparticles, as a solid phase, and is also well suited in particular to such systems that include a polyanion among the assay components.

A. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Acyl (and Other Chemical Structural Group Definitions)

As used herein, the term "acyl" refers to a —C(O)R$_a$ group where R$_a$ is hydrogen, alkyl, cycloalkyl, cycloalkylalkyl, phenyl or phenylalkyl. Representative examples of acyl include, but are not limited to, formyl, acetyl, cylcohexylcarbonyl, cyclohexylmethylcarbonyl, benzoyl, benzylcarbonyl and the like.

As used herein, the term "alkenyl" means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

As used herein, the term "alkyl radical" means any of a series of univalent groups of the general formula $C_nH_{2n+1}$ derived from straight or branched chain hydrocarbons.

As used herein, the term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkynyl" means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

As used herein, the term "amido" refers to an amino group attached to the parent molecular moiety through a carbonyl group (wherein the term "carbonyl group" refers to a —C(O)— group).

As used herein, the term "amino" means —$NR_bR_c$, wherein $R_b$ and $R_c$ are independently selected from the group consisting of hydrogen, alkyl and alkylcarbonyl.

As used herein, the term "aralkyl" means an aryl group appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

As used herein, the term "aryl" means a phenyl group, or a bicyclic or tricyclic fused ring system wherein one or more of the fused rings is a phenyl group. Bicyclic fused ring systems are exemplified by a phenyl group fused to a cycloalkenyl group, a cycloalkyl group, or another phenyl group. Tricyclic fused ring systems are exemplified by a bicyclic fused ring system fused to a cycloalkenyl group, a cycloalkyl group, as defined herein or another phenyl group. Representative examples of aryl include, but are not limited to, anthracenyl, azulenyl, fluorenyl, indanyl, indenyl, naphthyl, phenyl, and tetrahydronaphthyl. The aryl groups of the present disclosure can be optionally substituted with one-, two, three, four, or five substituents independently selected from the group consisting of alkoxy, alkyl, carboxyl, halo, and hydroxyl.

As used herein, the term "carboxy" or "carboxyl" refers to —$CO_2H$ or —$CO_2$.

As used herein, the term "carboxyalkyl" refers to a —$(CH_2)$—$CO_2H$ or —$(CH_2)$—$CO_2^-$ group where n is from 1 to 10.

As used herein, the term "cyano" means a —CN group.

As used herein, the term "cycloalkenyl" refers to a non-aromatic cyclic or bicyclic ring system having from three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Representative examples of cycloalkenyl groups include cyclohexenyl, octahydronaphthalenyl, norbornylenyl, and the like. The cycloalkenyl groups can be optionally substituted with one, two, three, four, or five substituents independently selected from the group consisting of alkoxy, alkyl, carboxyl, halo, and hydroxyl.

As used herein, the term "cycloalkyl" refers to a saturated monocyclic, bicyclic, or tricyclic hydrocarbon ring system having three to twelve carbon atoms. Representative examples of cycloalkyl groups include cyclopropyl, cyclopentyl, bicyclo[3.1.1]heptyl, adamantyl, and the like. The cycloalkyl groups of the present disclosure can be optionally substituted with one, two, three, four, or five substituents independently selected from the group consisting of alkoxy, alkyl, carboxyl, halo, and hydroxyl.

As used herein, the term "cycloalkylalkyl" means a —$R_dR_e$ group where $R_d$ is an alkylene group and $R_e$ is cycloalkyl group. A representative example of a cycloalkylalkyl group is cyclohexylmethyl and the like.

As used herein, the term "halogen" means a —Cl, —Br, —I or —F; the term "halide" means a binary compound, of which one part is a halogen atom and the other part is an element or radical that is less electronegative than the halogen, e.g., an alkyl radical.

As used herein, the term "hydroxyl" means an —OH group.

As used herein, the term "nitro" means a —$NO_2$ group.

As used herein, the term "oxoalkyl" refers to —$(CH_2)$—$C(O)R_a$, where $R_a$ is hydrogen, alkyl, cycloalkyl, cycloalkylalkyl, phenyl or phenylalkyl and where n is from 1 to 10.

As used herein, the term "phenylalkyl" means an alkyl group which is substituted by a phenyl group.

As used herein, the term "sulfo" means a —$SO_3H$ group.

As used herein, the term "sulfoalkyl" refers to a —$(CH_2)$—$SO_3H$ or —$(CH_2)$—$SO_3^-$ group where n is from 1 to 10.

b) Anion

As used herein, the term "anion" refers to an anion of an inorganic or organic acid, such as, but not limited to, hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, aspartic acid, phosphate, polyacrylic acid, trifluoromethansulfonic acid, trifluoroacetic acid and fluorosulfonic acid and any combinations thereof.

c) Antibody

As used herein, the term "antibody" refers to a protein consisting of one or more polypeptides substantially encoded by immunoglobulin genes or fragments of immunoglobulin genes, and encompasses polyclonal antibodies, monoclonal antibodies, and antigen-binding fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antigen-binding antibody fragments, e.g., single chain antibodies (scFv or others), can be produced/selected using phage display technology. The ability to express antibody fragments on the surface of viruses that infect bacteria (bacteriophage or phage) makes it possible to isolate a single binding antibody fragment, e.g., from a library of greater than 1010 nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

d) Hydrogen Peroxide Generating Enzyme

As used herein, the term "hydrogen peroxide generating enzyme" refers to an enzyme that is capable of producing as a reaction product the chemical compound having the molecular formula $H_2O_2$, i.e. hydrogen peroxide. Non-limiting examples of hydrogen peroxide generating enzymes are listed below in Table 1.

TABLE 1

| ACCEPTED COMMON NAME | IUBMB ENZYME NOMENCLATURE | PREFERRED SUBSTRATE |
|---|---|---|
| (R)-6-hydroxynicotine oxidase | EC 1.5.3.6 | (R)-6-hydroxynicotine |
| (S)-2-hydroxy acid oxidase | EC 1.1.3.15 | (S)-2-hydroxy acid |
| (S)-6-hydroxynicotine oxidase | EC 1.5.3.5 | (S)-6-hydroxynicotine |
| 3-aci-nitropropanoate oxidase | EC 1.7.3.5 | 3-aci-nitropropanoate |
| 3-hydroxyanthranilate oxidase | EC 1.10.3.5 | 3-hydroxyanthranilate |
| 4-hydroxymandelate oxidase | EC 1.1.3.19 | (S)-2-hydroxy-2-(4-hydroxyphenyl)acetate |
| 6-hydroxynicotinate dehydrogenase | EC 1.17.3.3 | 6-hydroxynicotinate |
| Abscisic-aldehyde oxidase | EC 1.2.3.14 | abscisic aldehyde |
| acyl-CoA oxidase | EC 1.3.3.6 | acyl-CoA |
| Alcohol oxidase | EC 1.1.3.13 | a primary alcohol |
| Aldehyde oxidase | EC 1.2.3.1 | an aldehyde |
| amine oxidase | | |
| amine oxidase (copper-containing) | EC 1.4.3.6 | primary monoamines, diamines and histamine |
| amine oxidase (flavin-containing) | EC 1.4.3.4 | a primary amine |
| aryl-alcohol oxidase | EC 1.1.3.7 | an aromatic primary alcohol (2-naphthyl)methanol 3-methoxybenzyl alcohol |
| aryl-aldehyde oxidase | EC 1.2.3.9 | an aromatic aldehyde |
| Catechol oxidase | EC 1.1.3.14 | Catechol |
| cholesterol oxidase | EC 1.1.3.6 | Cholesterol |
| Choline oxidase | EC 1.1.3.17 | Choline |
| columbamine oxidase | EC 1.21.3.2 | Columbamine |
| cyclohexylamine oxidase | EC 1.4.3.12 | Cyclohexylamine |
| cytochrome c oxidase | EC 1.9.3.1 | |
| D-amino-acid oxidase | EC 1.4.3.3 | a D-amino acid |
| D-arabinono-1,4-lactone oxidase | EC 1.1.3.37 | D-arabinono-1,4-lactone |
| D-arabinono-1,4-lactone oxidase | EC 1.1.3.37 | D-arabinono-1,4-lactone |
| D-aspartate oxidase | EC 1.4.3.1 | D-aspartate |
| D-glutamate oxidase | EC 1.4.3.7 | D-glutamate |
| D-glutamate(D-aspartate) oxidase | EC 1.4.3.15 | D-glutamate |
| dihydrobenzophenanthridine oxidase | EC 1.5.3.12 | dihydrosanguinarine |
| dihydroorotate oxidase | EC 1.3.3.1 | (S)-dihydroorotate |
| dihydrouracil oxidase | EC 1.3.3.7 | 5,6-dihydrouracil |
| dimethylglycine oxidase | EC 1.5.3.10 | N,N-dimethylglycine |
| D-mannitol oxidase | EC 1.1.3.40 | Mannitol |
| Ecdysone oxidase | EC 1.1.3.16 | Ecdysone |
| ethanolamine oxidase | EC 1.4.3.8 | Ethanolamine |
| Galactose oxidase | EC 1.1.3.9 | D-galactose |
| Glucose oxidase | EC 1.1.3.4 | β-D-glucose |
| glutathione oxidase | EC 1.8.3.3 | Glutathione |
| Glycerol-3-phosphate oxidase | EC 1.1.3.21 | sn-glycerol 3-phosphate |
| Glycine oxidase | EC 1.4.3.19 | Glycine |
| glyoxylate oxidase | EC 1.2.3.5 | Glyoxylate |
| hexose oxidase | EC 1.1.3.5 | D-glucose, D-galactose D-mannose maltose lactose cellobiose |
| hydroxyphytanate oxidase | EC 1.1.3.27 | L-2-hydroxyphytanate |
| indole-3-acetaldehyde oxidase | EC 1.2.3.7 | (indol-3-yl)acetaldehyde |
| lactic acid oxidase | | Lactic acid |
| L-amino-acid oxidase | EC 1.4.3.2 | an L-amino acid |
| L-aspartate oxidase | EC 1.4.3.16 | L-aspartate |
| L-galactonolactone oxidase | EC 1.3.3.12 | L-galactono-1,4-lactone |
| L-glutamate oxidase | EC 1.4.3.11 | L-glutamate |
| L-gulonolactone oxidase | EC 1.1.3.8 | L-gulono-1,4-lactone |
| L-lysine 6-oxidase | EC 1.4.3.20 | L-lysine |
| L-lysine oxidase | EC 1.4.3.14 | L-lysine |
| long-chain-alcohol oxidase | EC 1.1.3.20 | A long-chain-alcohol |
| L-pipecolate oxidase | EC 1.5.3.7 | L-pipecolate |
| L-sorbose oxidase | EC 1.1.3.11 | L-sorbose |
| malate oxidase | EC 1.1.3.3 | (S)-malate |
| methanethiol oxidase | EC 1.8.3.4 | Methanethiol |
| monoamino acid oxidase | | |
| N6-methyl-lysine oxidase | EC 1.5.3.4 | 6-N-methyl-L-lysine |
| N-acylhexosamine oxidase | EC 1.1.3.29 | N-acetyl-D-glucosamine N-glycolylglucosamine N-acetylgalactosamine N-acetylmannosamine. |
| NAD(P)H oxidase | EC 1.6.3.1 | NAD(P)H |
| nitroalkane oxidase | EC 1.7.3.1 | a nitroalkane |
| N-methyl-L-amino-acid oxidase | EC 1.5.3.2 | an N-methyl-L-amino acid |

TABLE 1-continued

| ACCEPTED COMMON NAME | IUBMB ENZYME NOMENCLATURE | PREFERRED SUBSTRATE |
|---|---|---|
| nucleoside oxidase | EC 1.1.3.39 | Adenosine |
| Oxalate oxidase | EC 1.2.3.4 | Oxalate |
| polyamine oxidase | EC 1.5.3.11 | 1-N-acetylspermine |
| polyphenol oxidase | EC 1.14.18.1 | |
| Polyvinyl-alcohol oxidase | EC 1.1.3.30 | polyvinyl alcohol |
| prenylcysteine oxidase | EC 1.8.3.5 | an S-prenyl-L-cysteine |
| Protein-lysine 6-oxidase | EC 1.4.3.13 | peptidyl-L-lysyl-peptide |
| putrescine oxidase | EC 1.4.3.10 | butane-1,4-diamine |
| Pyranose oxidase | EC 1.1.3.10 | D-glucose<br>D-xylose<br>L-sorbose<br>D-glucono-1,5-lactone |
| Pyridoxal 5'-phosphate synthase | EC 1.4.3.5 | pyridoxamine 5'-phosphate |
| pyridoxine 4-oxidase | EC 1.1.3.12 | Pyridoxine |
| pyrroloquinoline-quinone synthase | EC 1.3.3.11 | 6-(2-amino-2-carboxyethyl)-7,8-dioxo-1,2,3,4,5,6,7,8-octahydroquinoline-2,4-dicarboxylate |
| Pyruvate oxidase | EC 1.2.3.3 | Pyruvate |
| Pyruvate oxidase (CoA-acetylating) | EC 1.2.3.6 | Pyruvate |
| Reticuline oxidase | EC 1.21.3.3 | Reticuline |
| retinal oxidase | EC 1.2.3.11 | Retinal |
| Rifamycin-B oxidase | EC 1.10.3.6 | rifamycin-B |
| Sarcosine oxidase | EC 1.5.3.1 | Sarcosine |
| secondary-alcohol oxidase | EC 1.1.3.18 | a secondary alcohol |
| sulfite oxidase | EC 1.8.3.1 | Sulfite |
| superoxide dismutase | EC 1.15.1.1 | Superoxide |
| superoxide reductase | EC 1.15.1.2 | Superoxide |
| tetrahydroberberine oxidase | EC 1.3.3.8 | (S)-tetrahydroberberine |
| Thiamine oxidase | EC 1.1.3.23 | Thiamine |
| tryptophan α,β-oxidase | EC 1.3.3.10 | L-tryptophan |
| urate oxidase (uricase, uric acid oxidase) | EC 1.7.3.3 | uric acid |
| Vanillyl-alcohol oxidase | EC 1.1.3.38 | vanillyl alcohol |
| Xanthine oxidase | EC 1.17.3.2 | Xanthine |
| xylitol oxidase | EC 1.1.3.41 | Xylitol | e) Detectable Label

As used herein the term "detectable label" refers to any moiety that generates a measurable signal via optical, electrical, or other physical indication of a change of state of a molecule or molecules coupled to the moiety. Such physical indicators encompass spectroscopic, photochemical, biochemical, immunochemical, electromagnetic, radiochemical, and chemical means, such as but not limited to fluorescence, chemifluorescence, chemiluminescence, and the like. Preferred detectable labels include acridinium compounds such as an acridinium-9-carboximide having a structure according to Formula I as set forth in section B herein below, and an acridinium-9-carboxylate aryl ester having a structure according to Formula II as also set forth in section B herein below.

f) Test Sample

As used herein, the term "test sample" generally refers to a biological material being tested for and/or suspected of containing a target analyte, i.e., an analyte of interest, which may also contain leukocytes. The biological material may be derived from any biological source but preferably is a biological fluid likely to contain the target analyte. Examples of biological materials include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil, etc. An exemplary test sample is derived from whole blood, serum or plasma. The test sample may be used directly as obtained from the biological source or following a pretreatment to modify the character of the sample. For example, such pretreatment may include preparing plasma from blood, diluting viscous fluids and so forth. Methods of pretreatment may also involve centrifugation, filtration, precipitation, dilution, distillation, mixing, concentration, inactivation of interfering components, the addition of reagents, lysing, etc. If such methods of pretreatment are employed with respect to the test sample, such pretreatment methods are such that the target analyte remains in the test sample at a concentration proportional to that in an untreated test sample (e.g., namely, a test sample that is not subjected to any such pretreatment method(s)).

B. Methods for Decreasing Interference from Leukocytes

Non-optimal serum or plasma sample preparation techniques including, but not limited to, inadequate centrifugation, incomplete clotting time, and exposure to thermal stress, have been found to cause interferences in plasma or serum containing assay samples which lead to inaccurate readings in specific binding assays. It has now been found that addition of a polycationic derivative of dextran to a plasma or serum containing assay sample during the specific binding assay, decreases or eliminates interferences due to inadequate centrifugation, so that accurate readings can be obtained. The method is demonstrated to work well, for example, in immunoassays of TSH and free PSA as described herein. Whereas re-centrifugation of nonoptimally handled plasma and serum samples has also been demonstrated to be effective in decreasing interferences and restoring sensitivity and accuracy in sample measurement in specific binding assays for alpha fetal protein (AFP), Hepatitis B core antibody (HBcAb), Hepatitis B surface antibody (HBsAb), human immunodeficiency virus (HIV), and PIVKA-II, it is believed that addition of a polycationic derivative of dextran to plasma or serum containing assay samples during performance of specific binding assays for these analytes will also be useful in decreasing interferences due to nonoptimal sample preparation.

The polycationic derivative of dextran, which is for example a diethylaminoethyl ether of dextran such as diethylaminoethyl-dextran (DEAE-dextran, available for example from Sigma-Aldrich Co., Saint Louis, Mo., Sigma D9885), can be added during the immunoassay as a separate reagent. Alternatively, the polycationic derivative of dextran can be incorporated into an assay specific diluent, such as in a microparticle diluent as described herein below. The amount of the polycationic derivative of dextran used in an assay may vary depending on the type and molecular weight of the particular molecule used. Generally, however, the amount used is a quantity which is effective at achieving the desired result, i.e., eliminating interference, without detrimentally affecting other assay parameters (such as sensitivity, specificity, etc.). By way of example, polycationic derivatives of dextran at final concentrations ranging from about 0.0001% to about 2% weight/volume (wt/vol) may be used as effective amounts. More preferably, polycationic derivatives of dextran ranging from about 0.01% to about 0.5% wt/vol are used. Even more preferably, polycationic derivatives of dextran ranging from about 0.001% to about 2% wt/vol are used. For DEAE-dextran, concentrations of about 0.02% to about 0.5% (wt/vol) are preferred, and particularly about 0.02%, 0.05%, 0.1%, 0.2%, 0.25%, or 0.5% (wt/vol). While higher concentrations of a polycationic derivative of dextran may still be effective at decreasing interferences in the sample, it is believed that the resulting higher viscosity at higher concentrations may cause carryover, particularly in high throughput automated specific binding assay systems. However, a skilled artisan can readily determine upper limits of concentration useful in a particular assay.

The polycationic derivatives of dextran may be used in any type of specific binding assay that tests for the presence of an analyte (such as an antigen or antibody) in a test sample containing or derived from serum or plasma, including but not limited to sandwich and competitive type immunoassays. The immunoassay methods of the present disclosure can be carried out in any of a wide variety of formats. General reviews of immunoassays are available in METHODS IN CELL BIOLOGY VOLUME 37: ANTIBODIES IN CELL BIOLOGY, Asai, ed. Academic Press, Inc. New York (1993); and BASIC AND CLINICAL IMMUNOLOGY 7TH EDITION, Stites & Terr, eds. (1991), which are herein incorporated by reference in their entireties. A typical heterogeneous sandwich immunoassay employs a solid phase (as a solid support) to which is bound a first (capture) antibody reactive with at least one epitope on the target analyte. A second (detection) antibody is also reactive with at least one epitope on the target analyte. The second antibody may be conjugated to a detectable label that provides a signal that is measured after the detection antibody binds to the captured target analyte. Typically in such assays, the detectable label is used for detecting and/or quantitating the target analyte. Such labels include, without limitation, enzymatic, fluorescent, chemiluminescent, and radioactive labels. The manner of making and using all types of immunoassays, and the reagents and/or labeled reagents used in such assays are well known to routine practitioners in the art.

The methods can be applied, for example, to many analyte-specific binding assays, such as, but not limited to a TSH specific binding assay. The TSH specific binding assay can be for example a modified ARCHITECT® TSH assay format (Abbott Laboratories, Abbott Park, Ill. 60035-6050) wherein a polycationic derivative of dextran is added to the assay sample during the assay, i.e., before or during the incubation of the sample with the solid phase. Preferably the polycationic derivative of dextran is incorporated within the TSH assay diluent which is combined with the plasma or serum sample and the TSH antibody. Alternatively the polycationic derivative of dextran be incorporated in the diluent of the anti-TSH coated microparticles (hereinafter "microparticle diluent") which is combined with the plasma or serum sample. Similarly, the method can be applied to a free PSA specific binding assay. The free PSA specific binding assay can be for example a modified ARCHITECT® free PSA assay format wherein a polycationic derivative of dextran is added to the assay sample during the assay, i.e., before or during the incubation of the sample with the solid phase. Preferably the polycationic derivative of dextran is incorporated in the anti-PSA microparticle diluent, which is combined with the plasma or serum sample. The method can also be applied to a PIVKA-II specific binding assay. The PIVKA-II specific binding assay can be for example a modified ARCHITECT® PIVKA-II assay format wherein a polycationic derivative of dextran is added to the assay sample during the assay, i.e., before or during the incubation of the sample with the solid phase. For example, the polycationic derivative of dextran can be incorporated in the PIVKA-II assay diluent at about 0.05% (wt/vol), which is combined with the plasma or serum sample. Following similar principles, it will be appreciated that the ARCHITECT® assay format can be similar modified with the addition of DEAE-dextran to test for alpha fetal protein (AFP), Hepatitis B core antibody (HBcAb), Hepatitis B surface antibody (HBsAb), human immunodeficiency virus (HIV), and PIVKA-II.

i. Antibodies

The methods can be applied to immunoassays that may utilize reagents comprising a polyclonal or monoclonal antibody, a chimeric antibody, a human antibody, an affinity maturated antibody or fragments of said antibodies (such as an Fab'2 fragment) or combinations of polyclonal, monoclonal and antibody fragments. As those of skill in the art readily appreciate, antibodies can be prepared by any of a number of commercial services (e.g., Berkeley Antibody Laboratories, Bethyl Laboratories, Anawa, Eurogenetec, etc.).

In typical immunoassays, when a test sample containing the target analyte contacts the first antibody, the first antibody captures the target analyte. The target analyte is contacted with the second antibody resulting in the formation of an immunodetection complex consisting of the first antibody, target analyte and second antibody, and the complex is bound to the solid phase. The signal generated by the second (detection) antibody is proportional to the concentration of the target analyte as determined by the rate of formation (k1) of the immunodetection complex versus the rate of dissociation of the immunodetection complex (k2).

While monoclonal antibodies are highly specific to the analyte/antigen, a polyclonal antibody can preferably be used as each capture antibody to immobilize as much of the analyte/antigen as possible. A monoclonal antibody with inherently higher binding specificity for the analyte/antigen may then preferably be used for each detection antibody. In any case, when capture and detection antibodies are used, each recognizes non-overlapping epitopes on the target analyte, and preferably is capable of binding simultaneously to different epitopes on the target analyte, each without interfering with the binding of the other.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen. If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal. The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies (see, e.g., Coligan, et al. (1991) Unit 9, Current Protocols in Immunology, Wiley Interscience).

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

The methods described herein can be applied, for example, to a specific binding assay that measures a target analyte including but not limited to thyroid stimulating hormone (TSH), luteinizing hormone (LH), free prostate specific antigen (free PSA), alpha fetal protein, Hepatitis B core antibody, Hepatitis B surface antibody, human immunodeficiency virus (HIV), and PIVKA-II. It will be understood that the specificity of a particular binding assay for a particular target analyte is derived from the specificity of the antibody or antibodies used in the specific binding assay.

ii. Detection

The methods can be applied to immunoassays using different formats and detection systems but are especially useful as applied to a specific binding assay involving a magnetic or paramagnetic solid phase, such as particles, including microparticles. In an exemplary method, a specific binding assay uses magnetic microparticles such as carboxylated magnetic microparticles. Microparticles can be suspended in the mixture of soluble reagents and test sample or can be retained and immobilized by a support material. In the latter case, the microparticles on or in the support material are not capable of substantial movement to positions elsewhere within the support material. Alternatively, the microparticles can be separated from suspension in the mixture of soluble reagents and test sample by sedimentation or centrifugation. When the microparticles are magnetic or paramagnetic the microparticles can be separated from suspension in the mixture of soluble reagents and test sample by a magnetic field.

The methods of the present disclosure can be adapted for use in systems that utilize microparticle technology including automated and semi-automated systems wherein the solid phase comprises a microparticle. Such systems include those described in pending U.S. Pat. No. 425,651 and U.S. Pat. No. 5,089,424, which correspond to published EPO App. Nos. EP 0 425 633 and EP 0 424 634, respectively, and U.S. Pat. No. 5,006,309.

Accordingly, in a specific binding assay for target analyte, the methods involve adding a polycationic derivative of dextran to one or more test samples containing serum or plasma during incubation of the one or more serum- or plasma-containing samples with a solid phase coated with at least a first antibody capable of specifically binding the target analyte. The method may involve use of the polycationic derivative of dextran in a sandwich assay involving two or more antibodies specific for the target analyte. For example, the method may include forming a first complex by incubating the serum or plasma sample with a solid phase such as magnetic or paramagnetic microparticles coated with a first antibody capable of specifically binding to the target analyte, and an assay diluent comprising a polycationic derivative of dextran, for a time and under conditions sufficient to allow the target analyte present in the sample to bind to the antibody coated microparticles, wherein the period of time and conditions sufficient for such binding are readily determined by those of routine skill in the art.

The method may further involve forming a second complex by incubating the first complex with an acridinium labeled conjugate comprising an acridinium compound attached to a second antibody capable of specifically binding to the target analyte, for a time and under conditions sufficient to allow the conjugate to bind to the first complex; creating a chemiluminescent reaction in the second complex; and then measuring the chemiluminescent reaction as relative light units wherein the amount of target analyte in the plasma or serum containing sample is directly related to the measured relative light units. Creating a chemiluminescent reaction may involve, for example, i) providing a source of hydrogen peroxide to the antibody-antigen complexes; and ii) adding a basic solution to the mixture of step (i), such that measuring the chemiluminescent reaction involves measuring the light signal generated or emitted following the addition of the basic solution.

In any method according to the present disclosure and using an acridinium compound as the detectable label, preferably the acridinium compound is an acridinium-9-carboxamide. Specifically, the acridinium-9-carboxamide has a structure according to formula I:

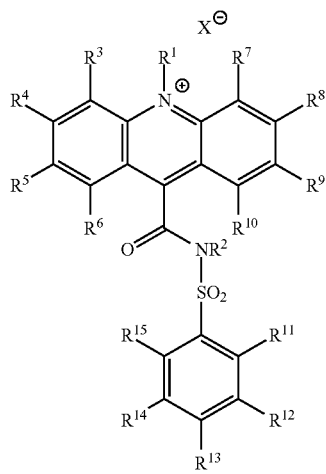

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\ominus$ is an anion.

Methods for preparing acridinium 9-carboxamides are described in Mattingly, P. G. *J. Biolumin. Chemilumin.*, 6, 107-14; (1991); Adamczyk, M.; Chen, Y.-Y., Mattingly, P. G.; Pan, Y. *J. Org. Chem.*, 63, 5636-5639 (1998); Adamczyk, M.; Chen, Y.-Y.; Mattingly, P. G.; Moore, J. A.; Shreder, K. *Tetrahedron*, 55, 10899-10914 (1999); Adamczyk, M.; Mattingly, P. G.; Moore, J. A.; Pan, Y. *Org. Lett.*, 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.*, 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.*, 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

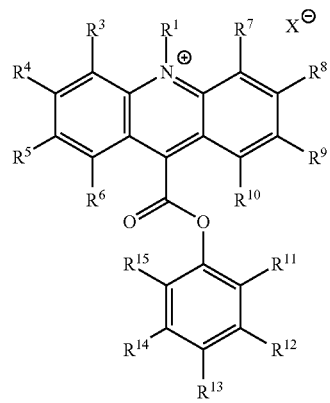

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.*, 4, 1111-21 (1965); Razavi, Z et al., *Luminescence*, 15:245-249 (2000); Razavi, Z et al., *Luminescence*, 15:239-244 (2000); and U.S. Pat. No. 5,241,070 (each incorporated herein by reference in their entireties for their teachings regarding same).

In addition to the at least one acridinium compound, the indicator solution can also contain at least one surfactant. Any surfactant that when dissolved in water, lowers the surface tension of the water and increases the solubility of organic compounds, can be used in the present invention. Examples of surfactants that can be used are one or more non-ionic or ionic surfactants (e.g., anionic, cationic or zwitterionic surfactants). Examples of non-ionic surfactants that can be used include, but are not limited to, t-octylphenoxypolyethoxyethanol (TRITON® X-100, Sigma Aldrich, St. Louis, Mo.), polyoxyethylenesorbitan monolaurate (TWEEN® 20), nonylphenol polyoxyethylene ether (NONIDET™ P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, TRITON® X-200, TRITON® QS 15, TRITON® QS 44, TRITON® XQS 20, TRIZMA® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Girard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, HYAMINE® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and LUVIQUAT™ FC370, LUVIQUAT™ HM 552, LUVIQUAT™ HOLD, LUVIQUAT™ MS 370, LUVIQUAT™ PQ 11PN and combinations thereof (all available from Sigma Aldrich, St. Louis, Mo.).

In a method using an acridinium label, the basic solution can be a solution having a pH of at least about 10. The source of hydrogen peroxide can be a buffer or a solution containing hydrogen peroxide. In an exemplary method, the source of hydrogen peroxide is a hydrogen peroxide generating enzyme. The hydrogen peroxide generating enzyme can be selected from the group of enzymes listed in Table 1 herein above and consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate (D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α, β-oxidase, urate oxidase (uricase, uric acid oxidase), vanillyl-alcohol oxidase, xanthine oxidase, xylitol oxidase and combinations thereof.

Optionally, the test sample may be treated prior to the addition of any one or more of the at least one basic solution, hydrogen peroxide source and detectable label. Such treatment may include dilution, ultrafiltration, extraction, precipitation, dialysis, chromatography and digestion. Such treatment may be in addition to and separate from any pretreatment that the test sample may receive or be subjected to as discussed previously herein. Moreover, if such treatment methods are employed with respect to the test sample, such treatment methods are such that the target analyte remains in the test sample at a concentration proportional to that in an untreated test sample (e.g., namely, a test sample that is not subjected to any such treatment method(s)).

The time and order in which the test sample, the at least one basic solution, source of hydrogen peroxide and the detectable label are added to form a mixture is not critical. Additionally, the mixture formed by the at least one basic solution, hydrogen peroxide source and the detectable label, can optionally be allowed to incubate for a period of time. For example, the mixture can be allowed to incubate for a period of time of from about 1 second to about 60 minutes. Specifically, the mixture can be allowed to incubate for a period of from about 1 second to about 18 minutes.

When a chemiluminescent detectable label is used, after the addition of the at least one basic solution, hydrogen peroxide source, and the detectable label to the test sample, a detectable signal, namely, a chemiluminescent signal, is generated. The signal generated by the mixture is detected for a fixed duration of time. Preferably, the mixture is formed and the signal is detected concurrently. The duration of the detection may range from about 0.01 to about 360 seconds, more preferably from about 0.1 to about 30 seconds, and most preferably from about 0.5 to about 5 seconds. Chemiluminescent signals generated can be detected using routine techniques known to those skilled in the art.

Thus, in a chemiluminescent immunoassay, a chemiluminescent detectable label is used and added to the test sample, the chemiluminescent signal generated after the addition of the basic solution and the detectable label indicates the presence of target analyte in the test sample, which signal can be detected. The amount or concentration of target analyte in the test sample can be quantified based on the intensity of the signal generated. Specifically, the amount of target analyte contained in a test sample is proportional to the intensity of the signal generated, and can be quantified based on comparing the amount of light generated to a standard curve for target analyte or by comparison to an analyte reference standard. The target analyte reference standard may comprise, for example, an anti-idiotypic antibody. The target analyte reference standard may comprise for example a derivatized target analyte, such as for example target analyte derivatized with a polyethylene glycol. The standard curve can be generated using serial dilutions or solutions to target analyte of known concentration, by mass spectroscopy, gravimetrically and by other techniques known in the art.

C. Kits

The present disclosure also provides kits for assaying test samples for presence of a target analyte wherein the test sample may contain other substances that interfere with immunodetection of the target analyte. Kits according to the present disclosure include one or more reagents useful for practicing one or more immunoassays according to the present disclosure. A kit generally includes a package with one or more containers holding the reagents, as one or more separate compositions or, optionally, as admixture where the compatibility of the reagents will allow. The kit can also include other material(s), which may be desirable from a user standpoint, such as a buffer(s), a diluent(s), a standard(s), and/or any other material useful in sample processing, washing, or conducting any other step of the assay. For example, according to the present disclosure, a kit for performing a specific binding assay of a sample containing plasma or serum, may include a container holding a solution of a polycationic derivative of dextran, such as DEAE-dextran, and instructions for quantifying the amount of a target analyte in the sample.

It can be useful for the kit to further contain a humanized monoclonal antibody, wherein the humanized monoclonal antibody is specific for the target analyte and be used as a positive control in specific binding assays as described herein. If desired, this component can be included in the kit in multiple concentrations to facilitate the generation of a standard curve to which the signal detected in the test sample can be compared. Alternatively, a standard curve can be generated by preparing dilutions of a single humanized monoclonal antibody solution provided in the kit.

Kits according to the present disclosure can include one or more first or capture antibodies, each of which binds to at least one epitope on the target analyte, and one or more second or detection antibodies, each of which binds to at least one epitope on the target analyte that is different from any epitope to which any of the capture antibodies bind, and further instructions for detecting or quantifying the target analyte. Kits according to the present disclosure may include a solid phase, to which the capture antibodies and/or detection antibodies are bound. The solid phase may comprise a material such as a magnetic or paramagnetic particle including a microparticle, a bead, a test tube, a microtiter plate, a cuvette, a membrane, a scaffolding molecule, a quartz crystal, a film, a filter paper, a disc or a chip. An exemplary kit contains magnetic or paramagnetic microparticles coated with the first (capture) antibody. The first antibody can comprise an antibody capable of specifically binding any target analyte, including but not limited to thyroid stimulating hormone (TSH), luteinizing hormone (LH), free prostate specific antigen (free PSA), alpha fetal protein, Hepatitis B core antibody, Hepatitis B surface antibody, human immunodeficiency virus (HIV) and PIVKA-II. A kit may contain non-human monoclonal antibodies against the target analyte, such as mouse monoclonal antibodies, and these may be used as capture and/or detection antibodies. For example, a kit for measuring the amount of TSH in a serum- or plasma-containing test sample may include a first antibody comprising a mouse, monoclonal anti-β TSH antibody, and a second antibody comprising a mouse, monoclonal anti-α TSH antibody.

Kits can be configured, for example, for performing a modified ARCHITECT® assay of any target analyte. For example, a kit for performing a modified ARCHITECT® assay of TSH, or of total or free prostate specific antigen (PSA), or of PIVKA-II, may for example include magnetic or paramagnetic microparticles coated with the appropriate analyte specific antibody, for example: an anti-TSH monoclonal antibody (one that is specific for TSH); or an anti-PSA monoclonal antibody (one that is specific for free PSA in the case of the free PSA assay, and one that binds both free and complexed PSA for the total PSA assay); or an anti-PIVKA-II monoclonal antibody (one that is specific for PIVKA-II), in a diluent that also contains a polycationic derivative of dextran such as DEAE-dextran.

1e;2qA kit may also include a detectable label that can be or is conjugated to each detection antibody. For example, a kit may include at least one direct label, which may be an enzyme, oligonucleotide, nanoparticle chemiluminophore, fluorophore, fluorescence quencher, chemiluminescence quencher, or biotin. In an exemplary embodiment, the direct label is an acridinium compound. For example, a kit may further include an acridinium-labeled conjugate comprising an acridinium compound attached to a second, detection antibody capable of specifically binding the target analyte. In the kit, the acridinium compound can be an acridinium-9-carboxamide having a structure according to formula I:

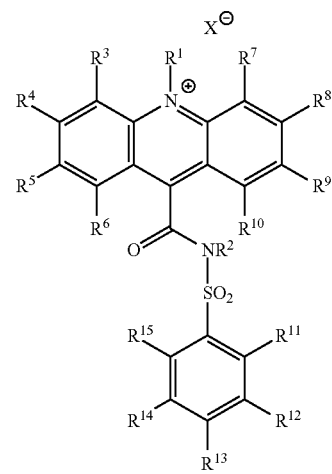

wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Alternatively, in kits using an acridinium compound, the acridinium compound can be an acridinium-9-carboxylate aryl ester having a structure according to formula II:

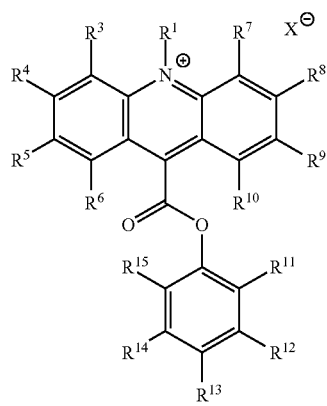

wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

Kits according to the present disclosure and which include an acridinium compound can also include a basic solution. For example, the basic solution can be a solution having a pH of at least about 10. Kits according to the present disclosure may further include a hydrogen peroxide source, such as a buffer solution, a solution containing hydrogen peroxide, or a hydrogen peroxide generating enzyme. For example, test kits may include an amount of a hydrogen peroxide generating enzyme as listed in Table 1 herein above and elsewhere herein, and combinations thereof.

Kits according to the present disclosure preferably include instructions for carrying out one or more of the immunoassays of the invention. Instructions included in kits of the present disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions. Moreover, the kits can be adapted for use in an automated system or semi-automated system.

An exemplary kit may thus contain components including but not limited to a first, anti-target analyte antibody, which may be a mouse, monoclonal antibody, which is coated on magnetic or paramagnetic microparticles in a buffer, preferably TRIS buffer, and even more preferably with protein (bovine) stabilizers and antimicrobial agents as a preservative. The kit may further contain an acridinium-labeled conjugate comprising a mouse anti-target analyte monoclonal antibody, preferably in MES (2-[N-Morpholino]ethanesulfonic acid) buffer with protein (bovine) stabilizers and antimicrobial agents as a preservative; and a modified assay diluent comprising a buffer, preferably TRIS, containing a polycationic derivative of dextran, preferably DEAE-dextran at a concentration ranging from about 0.01% wt/vol to about 0.5% wt/vol, or particularly about 0.02%, 0.05%, 0.1%, 0.2%, or 0.5% (wt/vol). Preferably the assay diluent also includes antimicrobial agents as preservatives. Alternatively, the polycationic derivative of dextran can be provided as a separate kit component for addition to the assay samples along with the assay diluent. A kit may also comprise a Multi-Assay Manual Diluent containing phosphate buffered saline solution with an antimicrobial agent as a preservative; a Pre-Trigger Solution containing 1.32% (wt/vol) hydrogen peroxide; a Trigger Solution containing 0.35 N sodium hydroxide; and a wash buffer containing phosphate buffered saline solution and an antimicrobial agent preservative.

D. Adaptations of the Methods of the Present Disclosure

By way of example, not of limitation, examples of the present invention shall now be given.

Example 1: Evaluation of Microparticle Overcoating Conditions and Evaluation of Candidate Additives Magnetic microparticles as used in the ARCHITECT® PIVKA-II assay format (Abbott Laboratories, Abbott Park, Ill., 60035-6050) were overcoated with various polymer additives: PLL, PAA, PVP, PEG, amino-PEG). Microparticle diluents containing various additives (ARCHITECT® TSH microparticles, non-magnetic microparticles, 2% (wt/vol) methylglycol chitosan, and 2% (wt/vol) DEAE-dextran) were prepared. Each microparticle and assay diluent was tested with both sufficiently centrifuged (Control) samples and insufficiently centrifuged (Test) samples. As shown in Tables 2A, 2B, 2C and 2D below, the value ratio (Test/Control) of the diluent containing DEAE-dextran was almost 100%. In contrast, under other conditions, substantial differences were observed between the value of control samples and test samples. The tables report the concentration of PIVKA-II (mAU/mL) obtained under the various conditions. In Tables 2B and 2D, E1-E5 refer to EDTA-treated plasma obtained from five different individuals.

TABLE 2A

| | Microparticle overcoat | | | | | |
|---|---|---|---|---|---|---|
| ID uP ASD | PLL uP Poly-L-lysin O/C uP SG3 | PAA uP PAA O/C uP SG3 | PVP uP PVP O/C uP SG3 | PEG uP PEG O/C uP SG3 | Amino uP Amino-PEG O/C uP SG3 | Amino2 uP Amino-PEG2 O/C uP SG3 |
| CAL A | 293 | 542 | 185 | 198 | 166 | 178 |
| CAL B | 1084 | 453 | 961 | 979 | 1001 | 1110 |
| CAL C | 1858 | 403 | 1742 | 1770 | 1750 | 1950 |
| CAL D | 2934 | 616 | 2705 | 2838 | 2917 | 3124 |
| CAL E | 13208 | 707 | 13109 | 13041 | 13741 | 14936 |
| CAL F | 940489 | 16892 | 787680 | 779059 | 791947 | 886717 |

TABLE 2B

| | | | Microparticle overcoat | | | |
|---|---|---|---|---|---|---|
| E1 Test | 129.9 | NA | 111.3 | 117.4 | 110.5 | 105.7 |
| E2 Test | 66.3 | NA | 60.0 | 66.0 | 59.5 | 71.6 |
| E3 Test | 91.1 | NA | 79.4 | 81.0 | 81.8 | 82.9 |
| E4 Test | 125.7 | NA | 125.7 | 118.1 | 121.7 | 112.5 |
| E5 Test | 133.2 | NA | 109.5 | 112.1 | 108.7 | 109.6 |
| E1 Control | 129.7 | NA | 117.9 | 122.4 | 109.5 | 112.6 |
| E2 Control | 123.0 | NA | 117.6 | 122.6 | 118.8 | 119.7 |
| E3 Control | 109.3 | NA | 105.6 | 108.6 | 104.5 | 107.1 |
| E4 Control | 162.3 | NA | 153.0 | 155.1 | 155.8 | 154.0 |
| E5 Control | 121.4 | NA | 114.0 | 116.4 | 116.5 | 119.0 |
| E1 (T/C) | 100.1% | NA | 94.4% | 96.0% | 101.0% | 93.9% |
| E2 (T/C) | 53.9% | NA | 51.0% | 53.8% | 50.1% | 59.8% |
| E3 (T/C) | 83.3% | NA | 75.1% | 74.6% | 78.3% | 77.4% |
| E4 (T/C) | 77.5% | NA | 82.2% | 76.1% | 78.1% | 73.1% |
| E5 (T/C) | 109.7% | NA | 96.1% | 96.3% | 93.3% | 92.2% |

TABLE 2C

| | | | Diluent additives | | | |
|---|---|---|---|---|---|---|
| ID uP ASD | +TSH uP +TSH uP SG3 | +Non-mag +Non-magnetic SG3 | 0% TritonX SG3 0% TritonX diluent | Chitosan Methyl-glycol chitosan SG3 | DEAE DEAE-dextran SG3 | Control SG3 |
| CAL A | 1716 | 189 | 238 | 257 | 188 | 174 |
| CAL B | 2465 | 902 | 962 | 587 | 1118 | 946 |
| CAL C | 3216 | 1658 | 1709 | 893 | 2002 | 1718 |
| CAL D | 4245 | 2644 | 2740 | 1240 | 3127 | 2718 |
| CAL E | 14371 | 12462 | 13039 | 5345 | 15596 | 12963 |
| CAL F | 837997 | 802263 | 853665 | 332663 | 968752 | 858658 |

TABLE 2D

| | | | Diluent additives | | | |
|---|---|---|---|---|---|---|
| E1 Test | 125.5 | 117.2 | 116.8 | 80.0 | 131.4 | 123.1 |
| E2 Test | 0.0 | 28.4 | 29.1 | 16.7 | 122.3 | 40.6 |
| E3 Test | 71.0 | 85.8 | 77.8 | 69.5 | 112.1 | 87.2 |
| E4 Test | 178.8 | 117.8 | 121.8 | 203.0 | 166.6 | 136.2 |
| E5 Test | 104.3 | 111.2 | 113.0 | 768.6 | 116.9 | 113.7 |
| E1 Control | 128.3 | 128.4 | 128.1 | 89.0 | 127.8 | 125.6 |
| E2 Control | 125.2 | 123.3 | 124.6 | 100.5 | 126.1 | 123.1 |
| E3 Control | 109.6 | 114.1 | 111.6 | 88.1 | 110.4 | 111.4 |
| E4 Control | 161.5 | 168.4 | 168.3 | 69.5 | 159.2 | 162.1 |
| E5 Control | 119.6 | — | 117.2 | 42.0 | 116.5 | 116.7 |
| E1 (T/C) | 97.8% | 91.3% | 91.2% | 89.9% | 102.8% | 97.9% |
| E2 (T/C) | 0.0% | 23.0% | 23.4% | 16.6% | 97.0% | 33.0% |
| E3 (T/C) | 64.7% | 75.1% | 69.7% | 78.9% | 101.6% | 78.3% |
| E4 (T/C) | 110.7% | 70.0% | 72.3% | 292.1% | 104.6% | 84.0% |
| E5 (T/C) | 87.2% | — | 96.4% | 1830.5% | 100.4% | 97.4% |

Example 2: ARCHITECT® PIVKA-II Assay Modified with DEAE-Dextran Diluent

The ARCHITECT® TSH assay (Abbott Laboratories, Abbott Park, Ill. 60035-6050) is a two-step immunoassay which determines the presence of thyroid stimulating hormone (TSH) in human serum and plasma using Chemiluminescent Microparticle Immunoassay (CMIA) technology with flexible assay protocols, referred to as CHEMIFLEX®. In the first step, a serum or plasma sample, anti-TSH antibody coated paramagnetic microparticles, and TSH Assay Diluent are combined. (The TSH Assay diluent contains 0.5 M TRIS HCl, 1.5 M TRIS base, 1.3 M NaCl, 0.2% of the antimicrobial agent NIPASEPT® (Nipa Laboratories Ltd., Wilmington Del.) and the antimicrobial agent A56620 (Abbott Laboratories, Abbott Park, Ill.), at pH 8.8). TSH present in the sample binds to the anti-TSH antibody coated microparticles. After washing, anti-TSH acridinium labeled conjugate is added as the second step. Two solutions referred to as a Pre-Trigger and Trigger Solution, which comprise hydrogen peroxide and sodium hydroxide, respectively, are then added to the reaction mixture and the resulting chemiluminescent reaction is measured as relative light units (RLUs). A direct relationship exists between the amount of TSH in the plasma or serum sample and RLUs detected by the ARCHITECT®/optical system.

A specific binding assay for PIVKA-II was conducted using a modified ARCHITECT® assay format (Abbott Laboratories, Abbott Park, Ill., 60035-6050) specific for PIVKA-II, wherein DEAE-dextran was added to the assay sample before incubation of the sample with the solid phase. The standard assay diluent was used for preparing one group of samples, and solutions containing 0%, 0.005%, 0.02% and 0.2% (wt/vol) DEAE-dextran were prepared and used as alternative assay diluents. Each assay diluent was tested with both sufficiently centrifuged (spun) samples and insufficiently centrifuged (unspun) samples. As shown in Tables 3A and 3B below, it was observed that unspun samples prepared with 0% DEAE-dextran gave a much lower value for PIVKA-II than that obtained with spun samples. Additionally, among samples prepared with DEAE-dextran in the assay diluent, spun samples and unspun samples provided comparable values for PIVKA-II.

TABLE 3A

| | 0.2% DEAE-dextran, 1% PAA | | | 0.02% DEAE-dextran, 1% PAA | | |
|---|---|---|---|---|---|---|
| | PIVKA-II (mAU/mL) | | | PIVKA-II (mAU/mL) | | |
| Sample ID | Spun | Unspun | % Diff | Spun | Unspun | % Diff |
| EDTA plasma-e4 | 141.5 | 136.8 | −3.3% | 138.9 | 138.3 | −0.4% |
| EDTA plasma-e5 | 148.2 | 145.9 | −1.5% | 149.4 | 149.3 | 0.0% |
| EDTA plasma-e6 | 136 | 135.4 | −0.4% | 133.2 | 131.2 | −1.5% |

TABLE 3B

| | 0.005% DEAE-dextran, 1% PAA | | | 0% DEAE-dextran, 1% PAA | | |
|---|---|---|---|---|---|---|
| | PIVKA-II (mAU/mL) | | | PIVKA-II (mAU/mL) | | |
| Sample ID | Spun | Unspun | % Diff | Spun | Unspun | % Diff |
| EDTA plasma-e4 | 134.1 | 126.2 | −5.9% | 137 | 113.5 | −17.2% |
| EDTA plasma-e5 | 146.6 | 137.7 | −6.1% | 142.5 | 85.2 | −40.2% |
| EDTA plasma-e6 | 134.1 | 128.3 | −4.3% | 136.6 | 93.5 | −31.5% |

Example 3: ARCHITECT® TSH Assay Modified with DEAE-Dextran Diluent

A specific binding assay for TSH was conducted using a modified ARCHITECT assay format (Abbott Laboratories, Abbott Park, Ill., 60035-6050), wherein poly-L-lysine was excluded from the regular formulation of TSH assay diluent, and DEAE-dextran was added to the assay sample before incubation of the sample with the solid phase. A first assay diluent consisting of the standard TSH assay diluent excluding poly-L-lysine was prepared, and a second assay diluent consisting of the first assay diluent (modified TSH assay diluent) but diluted 10 times and containing 0.05% (wt/vol) DEAE-dextran was also prepared. These were used as alternative assay diluents. Each assay diluent was tested with both sufficiently centrifuged (spun) samples and insufficiently centrifuged (unspun) samples. As shown in Table 4 below, it was observed that unspun samples prepared with 0% DEAE-dextran gave a much lower value for TSH than that obtained with spun samples. Additionally, among samples prepared with 0.05% (wt/vol) DEAE-dextran in the assay diluent, spun samples and unspun samples provided comparable values for TSH.

TABLE 4

| Sample ID | 0.05% DEAE, ×10 dil Modified TSH | | | Modified TSH | | |
|---|---|---|---|---|---|---|
| | TSH (ulU/mL) | | | TSH (ulU/mL) | | |
| | Spun | Unspun | % Diff | Spun | Unspun | % Diff |
| EDTA plasma-1 | 0.87 | 0.84 | −3.5% | 0.81 | 0.01 | −99.1% |
| EDTA plasma-2 | 1.61 | 1.47 | −8.7% | 1.37 | 0.01 | −99.4% |
| EDTA plasma-3 | 1.52 | 1.40 | −8.0% | 1.49 | 0.01 | −99.6% |
| | | | mean −6.71% | | | mean −99.36% |

One skilled in the art would readily appreciate that the methods and kits described in the present disclosure are well adapted to carry out the objects and obtain the ends and advantages mentioned, as well as those inherent therein. The methods, procedures, treatments, molecules, specific compounds and kits described herein are merely representative and exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. A method for detecting protein induced by vitamin K absence/antagonist-II (PIVKA-II) in a serum or plasma sample comprising leukocytes, the method comprising:
   (a) incubating a serum or plasma sample comprising leukocytes that is suspected of containing PIVKA-II with an assay diluent comprising from about 0.02% (wt/vol) to about 0.5% (wt/vol) diethylaminoethyl-dextran (DEAE-dextran) and a polyanion in solution, wherein poly-L-lysine is excluded from the diluent;
   (b) contacting the incubated sample of (a) with paramagnetic or magnetic microparticles coated with a first antibody capable of specifically binding to PIVKA-II for a time and under conditions sufficient to allow PIVKA-II present in the sample to bind to the antibody coated microparticles and form a first complex;
   (c) incubating the first complex with an acridinium labeled conjugate comprising an acridinium compound attached to a second antibody capable of specifically binding to PIVKA-II, for a time and under conditions sufficient to allow the conjugate to bind to the first complex, thereby forming a second complex;
   (d) creating a chemiluminescent reaction in the second complex; and
   (e) measuring the chemiluminescent reaction as relative light units wherein the amount of PIVKA-II in the plasma or serum sample is directly related to the measured relative light units, whereby PIVKA-II is detected in the plasma or serum sample and leukocyte interference is reduced.

2. The method of claim 1, wherein step (d) further comprises providing a source of hydrogen peroxide and a basic solution to the second complex.

3. The method of claim 2, wherein the basic solution is a solution having a pH of at least about 10.

4. The method of claim 2, wherein the source of hydrogen peroxide is a buffer or a solution containing hydrogen peroxide.

5. The method of claim 2, wherein the source of hydrogen peroxide is a hydrogen peroxide generating enzyme.

6. The method of claim 5, wherein the hydrogen peroxide generating enzyme is selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate (D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5′-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

7. The method of claim 1, wherein the first antibody is selected from the group consisting of a polyclonal antibody, a monoclonal antibody, a chimeric antibody, a human antibody, and an affinity maturated antibody.

8. The method of claim 1, wherein the second antibody is selected from the group consisting of a polyclonal antibody, a monoclonal antibody, a chimeric antibody, a human antibody, and an affinity maturated antibody.

9. The method of claim 1, wherein the acridinium compound is an acridinium-9-carboxamide having a structure

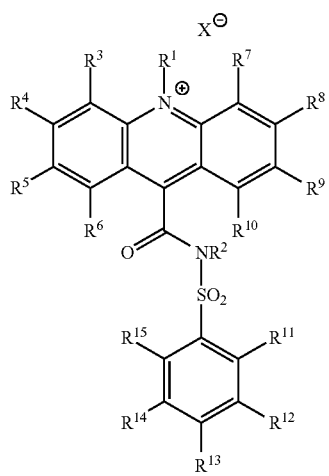

I according to formula I:
wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

10. The method of claim 1, wherein the acridinium compound is an acridinium-9-carboxylate aryl ester having a structure

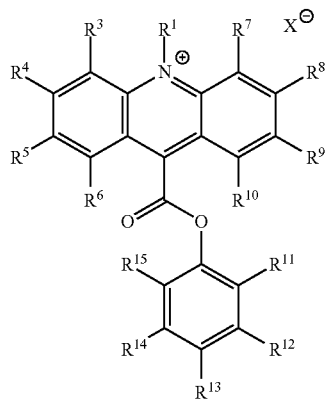

II according to formula II:
wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

11. The method of claim 1, wherein the polyanion is poly-acrylic acid.

* * * * *